(12) United States Patent
Ward

(10) Patent No.: US 9,207,176 B2
(45) Date of Patent: Dec. 8, 2015

(54) CONCENTRATION MEASUREMENT USING LUMINESCENCE

(75) Inventor: Geoffrey Ward, Warrnambool (AU)

(73) Assignee: Oxford Optronix LTD., Milton Park, Oxfordshire (GB)

( * ) Notice: Subject to any disclaimer, the term of this patent is extended or adjusted under 35 U.S.C. 154(b) by 49 days.

(21) Appl. No.: 13/811,182

(22) PCT Filed: Jul. 19, 2011

(86) PCT No.: PCT/GB2011/051358
§ 371 (c)(1),
(2), (4) Date: Jun. 7, 2013

(87) PCT Pub. No.: WO2012/010884
PCT Pub. Date: Jan. 26, 2012

(65) Prior Publication Data
US 2013/0256562 A1    Oct. 3, 2013

(30) Foreign Application Priority Data

Jul. 19, 2010   (GB) .................................. 1012078.0

(51) Int. Cl.
*G01N 21/64* (2006.01)
*G01N 21/77* (2006.01)

(52) U.S. Cl.
CPC ............ *G01N 21/64* (2013.01); *G01N 21/6408* (2013.01); *G01N 21/6428* (2013.01);
(Continued)

(58) Field of Classification Search
CPC .................. G01N 21/6408; G01N 2021/6432; G01N 21/6428; G01N 31/225; G01N 21/64
USPC ....................................................... 250/459.1
See application file for complete search history.

(56) References Cited

U.S. PATENT DOCUMENTS 4,810,655 A    3/1989  Khalil et al.
4,895,156 A *  1/1990  Schulze ........................ 600/342
(Continued)

FOREIGN PATENT DOCUMENTS

EP         0252578 A2    1/1988
WO    2004/102155 A2    11/2004

OTHER PUBLICATIONS

International Searching Authority, European Patent Office, "Notification of Transmittal of the International Search Report and the Written Opinion of the International Searching Authority, or the Declaration" for International application No. PCT/GB2011/051358, Oct. 25, 2011, 1 page.
(Continued)

*Primary Examiner* — Marcus Taningco
(74) *Attorney, Agent, or Firm* — McDonnell Boehnen Hulbert & Berghoff LLP

(57) ABSTRACT

A method of measuring the concentration of a substance, using a sensor (2) comprising a luminescent material, an LED light source (14) which supplies a pulse of light to the sensor to cause luminescence of the material, a detector (26) for detecting the emitted light and a data processing module (28) for analysing the signals and indicating the concentration of the substance. In a measuring sequence there is a series of pulses of light spaced apart sufficiently to permit the luminescence to decay between pulses. The signals which are analysed are those generated after each pulse of light has terminated and the luminescence is decaying. The data processing module (28) comprises a plurality of accumulators (52A, 52B, 52C and 52D) which are controlled to be operable over a corresponding plurality of different periods of time during decay of the luminescence. Each accumulator accumulates values indicative of the intensity of the luminescence from the series of pulses in the measuring sequence. The parameters regarding the accumulators are stored in a configuration memory (42) which is part of the sensor.

19 Claims, 6 Drawing Sheets

(52) U.S. Cl.
CPC ...... *G01N21/7703* (2013.01); *G01N 2021/641* (2013.01); *G01N 2021/6413* (2013.01); *G01N 2021/6434* (2013.01); *G01N 2021/772* (2013.01); *G01N 2021/773* (2013.01); *G01N 2021/7786* (2013.01)

(56) References Cited

U.S. PATENT DOCUMENTS

| | | | |
|---|---|---|---|
| 4,900,933 | A | 2/1990 | Nestor et al. |
| 5,039,219 | A | 8/1991 | James et al. |
| 5,315,993 | A * | 5/1994 | Alcala ............................ 600/341 |
| 6,051,437 | A * | 4/2000 | Luo et al. ....................... 436/172 |
| 6,531,097 | B1 * | 3/2003 | Vojnovic et al. ............ 422/82.07 |
| 2003/0099574 | A1 * | 5/2003 | Bentsen et al. ............. 422/82.07 |
| 2003/0190262 | A1 * | 10/2003 | Blazewicz et al. ............... 422/94 |
| 2007/0212792 | A1 | 9/2007 | Havens et al. |
| 2009/0075321 | A1 * | 3/2009 | Obeid et al. ..................... 435/29 |
| 2010/0018119 | A1 | 1/2010 | Lam et al. |

OTHER PUBLICATIONS

International Searching Authority, European Patent Office, "Patent Cooperation Treaty PCT International Search Report" for International application No. PCT/GB2011/051358, Oct. 25, 2011, 3 pages.

International Searching Authority, European Patent Office, "PCT Written Opinion of the International Searching Authority" for International application No. PCT/GB2011/051358, Oct. 25, 2011, 10 pages.

Sharman, K. K.; Periasamy, A.; H. Ashworth, H; Demas, J. N.; and Snow, N. H.; Error Analysis of the Rapid Lifetime Determination Method for Double-Exponential Decays and New Windowing Schemes, Analytical Chemistry, Mar. 1, 1999, pp. 947-952, vol. 71, No. 5.

Bacon, J.R.; and Demas, J. N., Determination of Oxygen Concentrations by Luminescence Quenching of a Polymer-Immobilized Transition-Metal Complex, Analytical Chemistry, Dec. 1, 1987, pp. 2780-2785, vol. 59, No. 23.

Woods, R.J.; Scypinski, S.; Cline Love, L.J., and Ashworth, H.A., Transient Digitizer for the Determination of Microsecond Luminescence Lifetimes, Analytical Chemistry, Jul. 1984, pp. 1395-1400, vol. 56, No. 8.

Ballew, R. M.; and Demas, J. N.; Error Analysis of the Rapid Lifetime Determination Method for Evaluation of Single Exponential Decays with a Non-Zero Baseline, Analytica Chimica Acta, 1991, pp. 121-127, vol. 245, Elsevier Science Publishers B.V., Amsterdam.

Young, W.K; Vojnovic, B.; and Wardman, P.; Measurement of oxygen tension in tumours by time-resolved fluorescence, British Journal of Cancer, 1996, pp. S256-S259, vol. 74, Suppl. XXVII.

* cited by examiner

| Iteration | | τ0 | τ1 | τ2 | τ3 | τ4 | Minimum | Uncertainty |
|---|---|---|---|---|---|---|---|---|
| 1 | Tau | 0.05 | 37.5375 | 75.025 | 112.5125 | 150 | | 149.95 |
| | SSQ | 14.47706 | 0.260633 | 0.117707 | 0.440605 | 0.677446 | 0.117707 | |
| 2 | Tau | 37.5375 | 56.28125 | 75.025 | 93.76875 | 112.5125 | | 74.975 |
| | SSQ | 0.260633 | 0.001743 | 0.117707 | 0.2864 | 0.440605 | 0.001743 | |
| 3 | Tau | 37.5375 | 46.90938 | 56.28125 | 65.65313 | 75.025 | | 37.4875 |
| | SSQ | 0.260633 | 0.040675 | 0.001743 | 0.043499 | 0.117707 | 0.001743 | |
| 4 | Tau | 46.90938 | 51.59531 | 56.28125 | 60.96719 | 65.65313 | | 18.74375 |
| | SSQ | 0.040675 | 0.006484 | 0.001743 | 0.01639 | 0.043499 | 0.001743 | |
| 5 | Tau | 51.59531 | 53.93828 | 56.28125 | 58.62422 | 60.96719 | | 9.371875 |
| | SSQ | 0.006484 | 0.001148 | 0.001743 | 0.007137 | 0.01639 | 0.001148 | |
| 6 | Tau | 51.59531 | 52.7668 | 53.93828 | 55.10977 | 56.28125 | | 4.6859375 |
| | SSQ | 0.006484 | 0.002995 | 0.001148 | 0.00078 | 0.001743 | 0.00078 | |
| 7 | Tau | 53.93828 | 54.52402 | 55.10977 | 55.69551 | 56.28125 | | 2.34296875 |
| | SSQ | 0.001148 | 0.000788 | 0.00078 | 0.001104 | 0.001743 | 0.00078 | |
| 8 | Tau | 54.52402 | 54.81689 | 55.10977 | 55.40264 | 55.69551 | | 1.171484375 |
| | SSQ | 0.000788 | 0.000741 | 0.00078 | 0.000901 | 0.001104 | 0.000741 | |
| 9 | Tau | 54.52402 | 54.67046 | 54.81689 | 54.96333 | 55.10977 | | 0.585742187 |
| | SSQ | 0.000788 | 0.000754 | 0.000741 | 0.00075 | 0.00078 | 0.000741 | |
| 10 | Tau | 54.67046 | 54.74368 | 54.81689 | 54.89011 | 54.96333 | | 0.292871094 |
| | SSQ | 0.000754 | 0.000745 | 0.000741 | 0.000743 | 0.00075 | 0.000741 | |
| 11 | Tau | 54.74368 | 54.78029 | 54.81689 | 54.8535 | 54.89011 | | 0.146435547 |
| | SSQ | 0.000745 | 0.000742 | 0.000741 | 0.000741 | 0.000743 | 0.000741 | |
| 12 | Tau | 54.78029 | 54.79859 | 54.81689 | 54.8352 | 54.8535 | | 0.073217773 |
| | SSQ | 0.000742 | 0.000742 | 0.000741 | 0.000741 | 0.000741 | 0.000741 | |

Figure 11

CONCENTRATION MEASUREMENT USING LUMINESCENCE

This invention relates to the measurement of the concentration of a substance using luminescence.

It is known to measure the concentration of a substance in living tissue, such as oxygen, using a probe which includes a luminescent component which is exposed to the substance. Light is directed to the component and the luminescent behaviour is analysed. That behaviour depends on the concentration of the substance, such as oxygen, which affects the intensity and duration of the luminescence. In the paper "Measurement of oxygen tension in tumours by time resolved fluorescence", By W. K. Young, B. Vojnovic and P. Wardman, British Journal of Cancer (1996) 74, (Suppl. XXVII) S256-S259, there is disclosed an arrangement in which a fluorophor, namely tris(4,7-diphenyl-1,10-phenanthroline) ruthenium chloride was incorporated in a polymer which was coated on the end of an optical probe. Pulses of light were supplied along an optical fibre from a laser and the exponential decay of the luminescence produced was analysed and used to determine the oxygen concentration.

In U.S. Pat. No. 6,531,097, with inventors B. Vojnovic, W. K. Young and P. Wardman, an alternative system is proposed. A light emitting diode (LED) is used as the light source and instead of analysing the decay of the luminescence, the system relies upon analysis of the increase in luminescence. This analysis takes place simultaneously with light being supplied. The analysis of the luminescence was carried out by the use of three or more integrating circuits, each producing an output representative of the input signal integrated over time. The light source is said to operate for a period of time which is substantially longer than the time during which the light emitted by the luminophor changes following the start of operation of the light source. Whilst the arrangement described is said to have the advantage that it is possible to use an LED rather than a laser, there are also disadvantages.

In U.S. Pat. No. 6,531,097, the measurement of the increase in luminescence intensity, simultaneously with operation of the excitation light source, has negative effects on the following:—signal to noise ratio; the stability of the intensity of the light source; and electro-magnetic noise created by switching the light source. The requirement that the light source operates for a time substantially longer than the time during which the luminescence changes, has a negative impact on the dynamic range of the detected signal and on the photo-bleaching of luminophores that have long lifetimes.

Viewed from a first aspect, the present invention provides a method of measuring the concentration of a substance, using a sensor comprising a luminescent material having a luminescent activity whose characteristics depend on the concentration of the substance, a light source which supplies a pulse of light to the sensor for a period of time sufficient to cause luminescence of the luminescent material, the luminescence rising to a peak and then decaying after the end of the pulse of light, a detector for detecting the luminescence and generating signals in response thereto, and a data processing module for analysing the signals and for providing data indicative of the concentration of the substance; wherein there is a measuring sequence comprised of a series of pulses of light spaced apart sufficiently to permit the luminescence to decay between the pulses, the signals which are analysed to provide the data indicative of the concentration of the substance are those generated after each pulse of light has terminated and the luminescence is decaying, and wherein the data processing module comprises a plurality of accumulators which are controlled to be operable over a corresponding plurality of different periods of time during the decay of the luminescence, each accumulator accumulating values indicative of the intensity of the luminescence from the series of pulses in the measuring sequence.

Thus, by contrast to the system of U.S. Pat. No. 6,531,097, the luminescence characteristic analysed is the decay of luminescence after the light pulse has terminated, rather than the rise in luminescence whilst the light pulse is operative.

As such, analysing the decay characteristics is known from the paper by Young et al. but the present invention uses an accumulation technique to provide the required data. This provides improved results and the method can be put into effect with an LED as the light source rather than a laser. Although each pulse from an LED results in a relatively small output of luminescence, there is a series of pulses and the outputs are accumulated. In some embodiments of the invention it is possible to eliminate readings when the accumulator may still retain a value from a previous pulse, or when the accumulator reaches saturation.

The periods of time over which the respective accumulators are active during the decay of luminescence after a pulse of light, are disposed at chosen points during the decay. The chosen points may depend on the substance whose concentration is being determined, and/or the range of concentrations that are expected. The rate of decay is steep initially, and then flattens out. Preferably there are at least two accumulators which are timed to be active in the steep part of the curve, and preferably these are closely adjacent to each other, with a first accumulator being active over a first period of time and a second accumulator being active over an adjacent period of time which commences on, or a relatively short time after, the end of the first period of time. Preferably, there is a third accumulator which is active over a third period of time, which commences a relatively long time after the end of the second period of time and thus when there is substantially smaller rate of decay of the luminescence than during the first and second periods of time. Preferably, there is a fourth accumulator which is active over a fourth period of time, which commences a relatively long time after the end of the third period of time and thus also when there is substantially smaller rate of decay of the luminescence than during the first and second periods of time.

The periods over which the respective accumulators are active may be determined by parameters stored in a configuration memory. Preferably there is a plurality of different sets of parameters, so that the appropriate set can be chosen having regard to the substance whose concentration is being determined, and/or the range of concentrations that are expected. In one arrangement, the configuration parameters are stored in a control unit to which the sensor is connected, the control unit including the data processing module. In this case, the appropriate set of parameters can be chosen manually. Alternatively, the sensor for a particular application may include an identifier such as an RFID chip, so that the control unit can detect the type of sensor and select the appropriate set of parameters.

Preferably, however, the configuration parameters are stored in a configuration memory which is part of the sensor itself, such as non volatile memory associated with the sensor. When the sensor is connected to the control unit, a connection is made with the configuration memory, and the configuration parameters are read and used by the data processing module. The connection could be a wireless connection. The configuration memory which forms part of the sensor may store a plurality of sets of configuration parameters appropriate for that sensor, which may be chosen as appropriate by the control unit.

A configuration memory which forms part of the sensor may store a variety of information, such as any or all of:
- sensor identification information
- sensor configuration information;
- the units of measurement for the assay substance;
- the energy or time exposure of the sensor;
- the allowed amount of energy or time exposure;
- the date of calibration of the sensor;
- the allowed period of time from the date of calibration of the sensor;
- the date of first use of the sensor;
- the allowed period of time from the date of first use of the sensor;
- the number of times that the sensor has been used;
- the allowed number of times that the sensor may be used;
- light pulsing and accumulator timings;
- minimum and maximum acceptable luminescent lifetimes;
- minimum and maximum acceptable sensor temperatures;
- minimum and maximum acceptable assay concentrations; and
- sensor dye and temperature calibration information.

Recording the allowed and actual energy or time exposure of the sensor allows the state of photo-bleaching to be monitored and the sensor to be flagged as due for replacement when required. In general there may be stored the value of a parameter relating to the life of the sensor, and the permitted maximum value of that parameter, for example in addition to or instead of the energy and/or time exposure and the permitted exposure, the date of calibration of the sensor and the allowed period of time from the date of calibration of the sensor; the date of first use of the sensor and the allowed period of time from the date of first use of the sensor; and the number of times that the sensor has been used and the allowed number of times that the sensor may be used.

A sensor which incorporates configuration memory may also incorporate a temperature measuring device, such as a thermocouple with a band-gap temperature sensor for cold junction correction. In such a case the configuration memory may also store any of the following data:
- Minimum and maximum un-calibrated cold junction temperatures;
- Minimum and maximum calibrated cold junction temperatures;
- Cold junction calibration information;
- Minimum and maximum thermocouple voltages;
- Minimum and maximum calibrated thermocouple temperatures;
- Thermocouple calibration information.

The use of a sensor with its own configuration memory allows the control unit to be configured for a wide range of different situations. For example, sensors may be optimised for different measurement ranges, luminescent lifetimes and even different assay substances, all measured by the same apparatus.

In some embodiments of the invention, the periods of time for which the accumulators are operable are separated from each other by intervals in which none of the accumulators is operable. The interval may if desired be longer than the respective period of time for which any accumulator is operable. In some embodiments of the invention, each period for which an accumulator is operable is spaced from the next period. However, in some embodiments there may be at least some periods which are adjacent with no interval or overlap. This may be the case at the start of the decay of luminescence where there is a sharp reduction in output and the periods may need to be close together. Whilst in some embodiments it could be the case that there are no intervals between any periods in a sequence, in some embodiments there will be an interval between at least one pair of consecutive periods. There may be at least two, or at least three, pairs of consecutive periods for which there are intervals between the periods of the pair.

Where there is an interval between two periods in which an accumulator is operable, the interval may greater than the duration either of the periods themselves.

Where there are intervals between periods for which respective accumulators are active, in some embodiments the interval is smallest (or non-existent) for a pair of periods nearest the peak of luminescence and greatest for a pair of periods furthest from the peak. In some embodiments of the invention, the interval between a pair of periods for which respective accumulators are active increases incrementally from a pair nearest the peak to a pair furthest from the peak.

Arrangements in which there is an interval between one period and the next period, differ from the system in U.S. Pat. No. 6,531,097 where the individual accumulators operate over adjacent periods of time. Thus, in the described embodiment of U.S. Pat. No. 6,531,097 a first accumulator operates over period t0 to t1; a second accumulator operates over period t1 to t2; and a third accumulator operates over period t2 to t3. The requirement that the integrating periods are consecutive has a negative impact on the noise and accuracy of the results. In embodiments of the present invention, accumulation may be carried out over time periods positioned as required during the decay phase of the luminescence.

In preferred embodiments of the invention, the periods of time over which the respective accumulators are operable are of substantially equal duration.

In some embodiments of the invention the duration of each period for which an accumulator is operable is substantially less than the time between the commencement of the first period and the end of the last period. In some embodiments of the invention the duration of each period for which an accumulator is operable is substantially less than the time between the peak of luminescence after a pulse and the commencement of the next pulse. In some embodiments of the invention the duration of each period for which an accumulator is operable is substantially less than the time for the luminescence to decay after a pulse.

In some embodiments of the invention, the duration of each period for which an accumulator is operable is no more than about 5% of the time between the commencement of the first period and the end of the last period; in some embodiments of the invention, the duration of each period for which an accumulator is operable is no more than about 4% of the time between the commencement of the first period and the end of the last period; in some embodiments of the invention, the duration of each period for which an accumulator is operable is no more than about 3% of the time between the commencement of the first period and the end of the last period; in some embodiments of the invention, the duration of each period for which an accumulator is operable is no more than about 2% of the time between the commencement of the first period and the end of the last period.

In some embodiments of the invention, the duration of each period for which an accumulator is operable is no more than about 5% of the time between the peak of luminescence after a pulse and the commencement of the next pulse; in some embodiments of the invention, the duration of each period for which an accumulator is operable is no more than about 4% of the time between the peak of luminescence after a pulse and the commencement of the next pulse; in some embodiments of the invention, the duration of each period for which an accumulator is operable is no more than about 3% of the time between the peak of luminescence after a pulse and the commencement of the next pulse; in some embodiments of the invention, the duration of each period for which an accumulator is operable is no more than about 2% of the time between the peak of luminescence after a pulse and the commencement of the next pulse.

In some embodiments of the invention, the duration of each period for which an accumulator is operable is no more than about 5% of the time for the luminescence to decay after a pulse; in some embodiments of the invention, the duration of each period for which an accumulator is operable is no more than about 4% of the time for the luminescence to decay after a pulse; in some embodiments of the invention, the duration of each period for which an accumulator is operable is no more than about 3% of the time for the luminescence to decay after a pulse; in some embodiments of the invention, the duration of each period for which an accumulator is operable is no more than about 2% of the time for the luminescence to decay after a pulse.

In some embodiments of the invention, the time for the luminescence to decay after a pulse is taken as the time for the luminescence to decay to about 20% of the peak value after a pulse; in some embodiments of the invention, the time for the luminescence to decay after a pulse is taken as the time for the luminescence to decay to about 15% of the peak value after a pulse; in some embodiments of the invention, the time for the luminescence to decay after a pulse is taken as the time for the luminescence to decay to about 10% of the peak value after a pulse; in some embodiments of the invention, the time for the luminescence to decay after a pulse is taken as the time for the luminescence to decay to about 5% of the peak value after a pulse; in some embodiments of the invention, the time for the luminescence to decay after a pulse is taken as the time for the luminescence to decay to a value less than about 5% of the peak value after a pulse.

In some embodiments of the invention, the time for the luminescence to decay from the peak after a pulse is at least about 75 microseconds; in some embodiments of the invention, the time for the luminescence to decay from the peak after a pulse is at least about 80 microseconds; in some embodiments of the invention, the time for the luminescence to decay from the peak after a pulse is at least about 90 microseconds; in some embodiments of the invention, the time for the luminescence to decay from the peak after a pulse is at least about 100 microseconds; in some embodiments of the invention, the time for the luminescence to decay from the peak after a pulse is at least about 120 microseconds; in some embodiments of the invention, the time for the luminescence to decay from the peak after a pulse is at least about 140 microseconds; in some embodiments of the invention, the time for the luminescence to decay from the peak after a pulse is at least about 200 microseconds; in some embodiments of the invention, the time for the luminescence to decay from the peak after a pulse is at least about 250 microseconds; in some embodiments of the invention, the time for the luminescence to decay from the peak after a pulse is at least about 300 microseconds.

In some embodiments of the invention, the time between the peak of luminescence after a pulse and the commencement of the next pulse is at least about 75 microseconds; in some embodiments of the invention, the time between the peak of luminescence after a pulse and the commencement of the next pulse is at least about 80 microseconds; in some embodiments of the invention, the time between the peak of luminescence after a pulse and the commencement of the next pulse is at least about 90 microseconds; in some embodiments of the invention, the time the time between the peak of luminescence after a pulse and the commencement of the next pulse is at least about 100 microseconds; in some embodiments of the invention, the time between the peak of luminescence after a pulse and the commencement of the next pulse is at least about 120 microseconds; in some embodiments of the invention, the time between the peak of luminescence after a pulse and the commencement of the next pulse is at least about 140 microseconds; in some embodiments of the invention, the time between the peak of luminescence after a pulse and the commencement of the next pulse is at least about 200 microseconds; in some embodiments of the invention, the time between the peak of luminescence after a pulse and the commencement of the next pulse is at least about 250 microseconds; in some embodiments of the invention, the time between the peak of luminescence after a pulse and the commencement of the next pulse is at least about 300 microseconds.

In some embodiments of the invention, the duration of each period for which an accumulator is operable is no more than about 5 microseconds; in some embodiments of the invention, the duration of each period for which an accumulator is operable is no more than about 4 microseconds; in some embodiments of the invention, the duration of each period for which an accumulator is operable is no more than about 3 microseconds; in some embodiments of the invention, the duration of each period for which an accumulator is operable is no more than about 2 microseconds; in some embodiments of the invention, the duration of each period for which an accumulator is operable is between about 1 and 3 microseconds; in some embodiments of the invention, the duration of each period for which an accumulator is operable is between about 1.5 and 2.5 microseconds; in some embodiments of the invention, the duration of each period for which an accumulator is operable is about 2 microseconds.

In some embodiments of the invention, the time between pulses in the series is at least about 75 microseconds; in some embodiments of the invention, the time between pulses in the series is at least about 80 microseconds; in some embodiments of the invention, the time between pulses in the series is at least about 90 microseconds; in some embodiments of the invention, the time between the time between pulses in the series is at least about 100 microseconds; in some embodiments of the invention, the time between pulses in the series is at least about 120 microseconds; in some embodiments of the invention, the time between pulses in the series is at least about 140 microseconds; in some embodiments of the invention, the time between pulses in the series is at least about 200 microseconds; in some embodiments of the invention, the time between pulses in the series is at least about 250 microseconds; in some embodiments of the invention, the time between pulses in the series is at least about 300 microseconds.

In some embodiments of the invention, the duration of each period for which an accumulator is operable is relatively short. In some embodiments of the invention, the duration of each period for which an accumulator is operable can be relatively long, this being particularly the case if the periods are equal.

In some embodiments of the invention there are at least three accumulators; in some embodiments of the invention there are at least four accumulators; in some embodiments of the invention there are at least five accumulators.

In some embodiments of the invention there is an accumulator operable for a first period shortly after the peak of the luminescence, an accumulator operable for a second period shortly before the end of the decay of the luminescence (or shortly before the next light pulse), and at least one accumulator operable for a period arranged between the first and second periods. Preferably there is an accumulator operable for a period arranged between the first and second periods and which is spaced from both of the first and second periods. By shortly after the peak of the luminescence may mean within no more than about 5 microseconds of the peak; or no more than about 4 microseconds of the peak; or no more than about 3 microseconds of the peak; or no more than about 2 microseconds of the peak; or no more than about 1 microseconds of the peak; or no more than about 0.5 microseconds of the peak. By shortly before the end of the decay of the luminescence may mean within no more than about 50 microseconds of the end; or no more than about 40 microseconds of the end; or no more than about 30 microseconds of the end; or no more than about 20 microseconds of the end; or no more than about 10 microseconds of the end. In some embodiments the end of the decay may be taken as the time for the luminescence to decay to about 20% of the peak value after a pulse; in some embodiments of the invention, the end of the decay may be taken as the time for the luminescence to decay to about 15% of the peak value after a pulse; in some embodiments of the invention, the end of the decay may be taken as the time for the luminescence to decay to about 10% of the peak value after a pulse; in some embodiments of the invention, the end of the decay may be taken as the time for the luminescence to decay to about 5% of the peak value after a pulse; in some embodiments of the invention, the end of the decay may be taken as the time for the luminescence to decay to a value less than about 5% of the peak value after a pulse.

In implementation of some embodiments of the invention, the light source is pulsed for set periods of time. The light pulse is filtered in order to more closely approximate a narrow band light source and is conducted to a sensor comprising a luminophor, for example along a fibre optic. The luminescence from the luminophor is then gathered and conducted back to the instrument where it is filtered to remove traces of the original light source. The remaining light, that is the luminescence from the luminophor, is conducted back to a light sensing device where it is converted to an electrical signal. The electrical signal is coarsely corrected for ambient light and amplified. The signal is then switched to a number of accumulators. The timing of the light pulses and switching to the various accumulators is controlled by timing logic. The accumulation time for each area is constant, but the areas can be distributed after the light pulse completes as required. The distribution of integration areas is typically determined by mathematical modelling which includes the sensor lifetime characteristics and the measurement range required in order to maximise accuracy and minimise noise.

The sequence of light pulsing and accumulation is preferably repeated during an acquisition phase. Typically, there will be a "measurement pulse" followed by a "wait for completion" time, before an "interrupt pulse" and "A to D conversion" time. This is implemented to allow the final light pulse and integration periods to complete before initiating the measurement.

In one embodiment of the invention, the majority of a cycle, for example at least about 80% or at least about 90%, is taken up by the accumulators acquiring data. This is then followed by a short period, typically 5% of the cycle, when no pulses or integration take place. This allows the final accumulator value to be measured and recorded by an Analogue to Digital (A to D) converter and processor. There could be a software accumulator with A-D sampling at 10 MHz, for example. Finally a short reset phase, typically 5% of the cycle, allows the accumulators to be reset to a zero value. A typical cycle would be 1 second.

In a second embodiment of the invention the accumulator values are sampled at a fixed rate through the duration of the cycle. The linear slope through the samples acquired is proportional to the end value of the integration obtained in the first embodiment. The advantages of this method are:—

1) Samples immediately after the accumulator is reset can be rejected from the calculation of the slope to reduce the effect of the dielectric absorption of the capacitors used in the accumulators;
2) Samples greater than a threshold, corresponding to the saturation of the accumulator, can be rejected from the calculation of slope, thus increasing the practical dynamic range;
3) Oversampling and line fitting to the integral slope increases the effective resolution of the A to D converter and reduces quantisation noise;
4) Measurements are spread over the range of the A to D converters, thus potentially reducing some of the effects due to the inherent non-linearity of an A to D converter.

Thus, in a preferred embodiment of the invention, for each accumulator the accumulator value is sampled at intervals during the measurement sequence, and the values are processed to provide a slope which is used in determination of the substance concentration.

Preferably, the periods of time for which respective accumulators are operable are separated from each other by intervals in which none of the accumulators is operable. Preferably for at least one pair of periods of time for which the accumulators are operable, those periods are separated from each other by an interval in which none of the accumulators is operable, said interval being longer than the respective periods of time for which any of the accumulators is operable. In such an arrangement, the method may involve any of the optional features discussed above in connection with the method of the first aspect of the invention.

In another embodiment of the invention, two measurement circuits are alternated between acquisition phases and reset phases. In practice this can be implemented by allowing the light and integration pulses to continue for the whole cycle, while holding alternate channels in reset. In such an arrangement the integral values may be calculated using the slope method described above This allows a higher sampling rate with the ability to calculate the exponential lifetime a plurality of times during the measurement cycle rather than once per measurement cycle and without dropping data sampling.

Thus, in some embodiments of the invention, the data processing module comprises two channels, each of which comprises a plurality of accumulators which are controlled to be operable over a corresponding plurality of periods of time during decay of the luminescence, each accumulator accumulating values indicative of the intensity of the luminescence from the series of pulses in the measuring sequence, and wherein the measuring sequences are alternated between the two channels, the accumulators in one channel being reset after the end of the measuring sequence using that channel, whilst a measuring sequence is carried out using the other channel.

Thus, whilst the accumulators in one channel are being reset and waiting to become operable, the accumulators in the other channel are operable. In this manner the channels alternate.

In some embodiments of the invention, the periods of time for which the respective accumulators in a channel are operable are separated from each other by intervals in which none of the accumulators is operable. In some embodiments of the invention, for each accumulator the accumulator value is sampled at intervals during the period for which the accumulator is operable, and the values are processed to provide a slope which is used in determination of the substance concentration.

In implementation of embodiments of aspects of the invention, whether using final accumulator values or slopes obtained from regular sampling of values from the accumulators, the data analysis may utilise a modified least squares method developed specifically for use in accordance with the invention in order to calculate the exponential lifetime.

The invention also extends to apparatus constructed and configured to carry out the methods of the invention, including as options the optional features of the invention as discussed above.

Thus, viewed from a further aspect, the invention provides apparatus for measuring the concentration of a substance, comprising a sensor comprising a luminescent material having a luminescent activity whose characteristics depend on the concentration of the substance, a light source which supplies a pulse of light to the sensor for a period of time sufficient to cause luminescence of the luminescent material, the luminescence rising to a peak and then decaying after the end of the pulse of light, a detector for detecting the light emitted by the luminescence of the luminescent material and generating signals in response thereto, and a data processing module for analysing the signals and for providing data indicative of the concentration of the substance; wherein the data processing module is configured so that in a measuring sequence there is a series of pulses of light spaced apart sufficiently to permit the luminescence to decay between pulses, the signals which are analysed to provide the data indicative of the concentration of the substance are those generated after each pulse of light has terminated and the luminescence is decaying, and wherein the data processing module comprises a plurality of accumulators which are controlled to be operable over a corresponding plurality of different periods of time during decay of the luminescence, each accumulator accumulating values indicative of the intensity of the luminescence from the series of pulses in the measuring sequence.

The invention also extends to a software product for configuring a data processing module of apparatus for measuring the concentration of a substance, the apparatus comprising a sensor comprising a luminescent material having a luminescent activity whose characteristics depend on the concentration of the substance, a light source which supplies a pulse of light to the sensor for a period of time sufficient to cause luminescence of the luminescent material, the luminescence rising to a peak and then decaying after the end of the pulse of light, and a detector for detecting the light emitted by the luminescence of the luminescent material and generating signals in response thereto, the data processing module being for analysing the signals and for providing data indicative of the concentration of the substance, wherein the software product contains instructions which when run on the data processing module will cause the data processing module to operate so that in a measuring sequence there is a series of pulses of light spaced apart sufficiently to permit the luminescence to decay between pulses, the signals which are analysed to provide the data indicative of the concentration of the substance are those generated after each pulse of light has terminated and the luminescence is decaying, and wherein the data processing module comprises a plurality of accumulators which are controlled to be operable over a corresponding plurality of different periods of time during decay of the luminescence, each accumulator accumulating values indicative of the intensity of the luminescence from the series of pulses in the measuring sequence.

The software product may be in the form of physical media carrying the software, such as a CD, DVD, HDD, FDD or solid state memory module. Alternatively, the software product may be in the form of data provided from a remote location using suitable communications, such as over a network, for example the Internet.

Certain preferred embodiments of the invention will now be described, by way of example only, with reference to the accompanying drawings, in which:

FIG. 11 is a table showing part of the implementation of a method in accordance with the invention.

Figure 1:
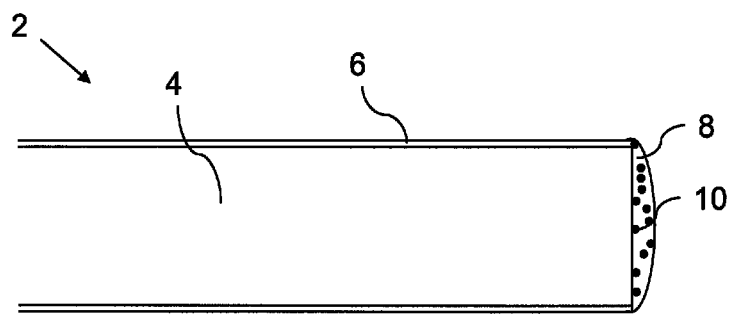
FIG. 1 is a partial cross-section through a sensor probe forming part of sensing apparatus embodying the invention.

FIG. 1 shows a sensor probe 2 comprising an optical fibre core 4 surrounded by a protective cladding layer 6. The optical fibre has a typical diameter of approximately 200 micrometers. At its tip it has a convex-curved polymer layer 8 having embedded within it a number of silica-gel particles 10, of average diameter 5 micrometers. The particles 10 have an oxygen sensitive luminophor such as ruthenium-chloride luminescent dye adsorbed on their surfaces.

Figure 2:
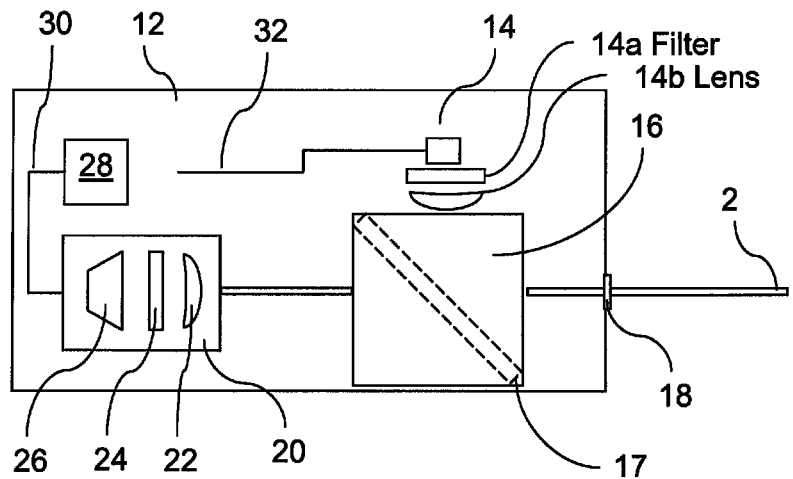
FIG. 2 is schematic diagram of the sensing apparatus.

FIG. 2 shows the sensor probe 2 connected via a port 18 to a base unit 12. The base unit 12 contains a light-emitting unit 14 comprising a light-emitting diode (LED) and, for example, a 450 nm filter 14a and a lens 14b. The filtering is preferably such that the light source approximates a narrow-band light source. The light-emitting unit 14 feeds into a beam splitter 16, to which the sensor probe 2 and a receiver unit 20 are optically-connected. The beam splitter 16 includes a dichroic filter 17 which reflects the light from the LED through the port 18 to the sensor probe 2, and then passes the luminescence light from the sensor probe 2 to the receiver unit 20. The receiver unit 20, which may be an integrated component, comprises a coupling lens 22, a long-pass filter 24 and a photo-detector 26 such as a photomultiplier tube or avalanche photodiode, for example. The base unit 12 further contains a controller 28 which is electronically connected to the light-emitting unit 14, by a connection 32, and to the photo-detector 26, by a connection 30. The components of the base unit 12 may all be within a common housing or may be distributed.

In use, the controller 28 signals along the connection 32 to the light-emitting unit 14 to cause an emission of light. This passes through the beam splitter 16 to the probe 2. On reaching the polymer layer 8, the light causes the dye on the silica-gel particles 10 to luminesce. The luminescence response is dependent on the oxygen concentration at the tip of the probe 2. Light from the luminescence travels down the sensor probe 2 towards the base unit 12. It passes through the beam splitter 16 towards the receiver unit 20. Inside the receiver unit 20, it passes through the coupling lens 22 and long-pass filter 24 before entering the photo-detector 26. The long-pass filter 24 removes any stray light not due to the luminescence, which might typically peak at around 600 nm and, for example, the long-pass filter 24 may be a 590 nm acetate filter. The electrical signal from the photo-detector 26 passes along the connection 30 to the controller 28 where it is received and processed as described below.

Figure 3:
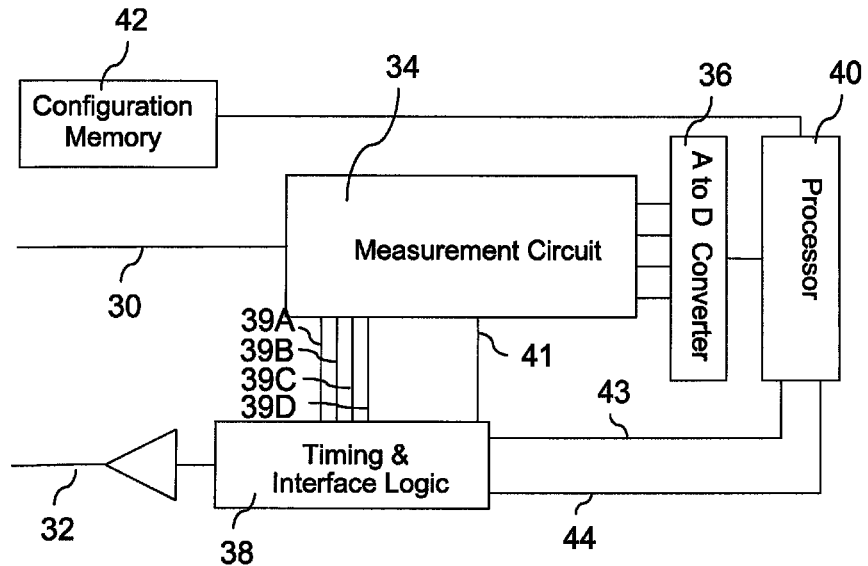
FIG. 3 is a schematic diagram of components within the sensing apparatus.

FIG. 3 figuratively shows the main components of the controller 28. The connection 30 from the photo-detector 26 is received in an analogue measurement circuit 34. The measurement circuit 34 feeds into an analogue-to-digital (A to D) converter 36 which in turn feed into a processor 40. Timing and interface logic 38 connects to the measurement circuit 34 by accumulator control lines 39A-39D and a reset control line 41. The timing and interface logic 38 communicates with the processor 40 by a data ready control line 43 and a timing state/configuration connection 4; and has a connection 32 leading to the light-emitting unit 14. A configuration memory 42, which may be volatile or non-volatile, having, for example, a magnetic, optical or silicon storage medium, is readable by the processor 40 to determine configuration settings for the apparatus.

Figure 4:
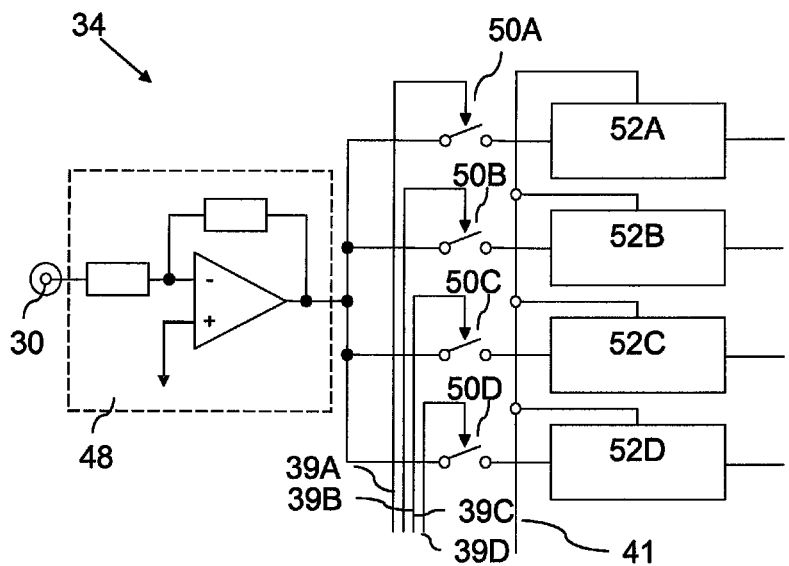
FIG. 4 is a circuit diagram of a measurement circuit component.

FIG. 4 shows the measurement circuit 34 in more detail. The connection 30 from the photo-detector 26 passes through an amplifier 48 and is then split into four paths. Each path contains a high-speed electronic switch 50A-50D, controlled by the timing and interface logic 38, before leading into a respective accumulator 52A-52D.

Figure 5:
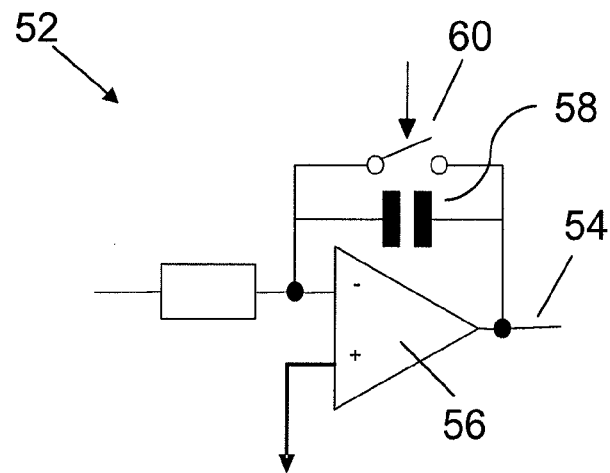
FIG. 5 is a circuit diagram of a sub-component of the measurement circuit.

FIG. 5 shows a detailed view of one of the identical accumulators 52A-52D. Each accumulator is a conventional operational-amplified accumulator circuit, the output of which is the integral of the input voltage over time. It comprises an operational amplifier 56 with a capacitor 58 between its non-inverting input lead and its output lead, as well as an electronic reset switch 60 arranged to discharge the capacitor 58 when closed. The reset switch 60 is controlled by the timing and interface logic 38.

Figure 6:
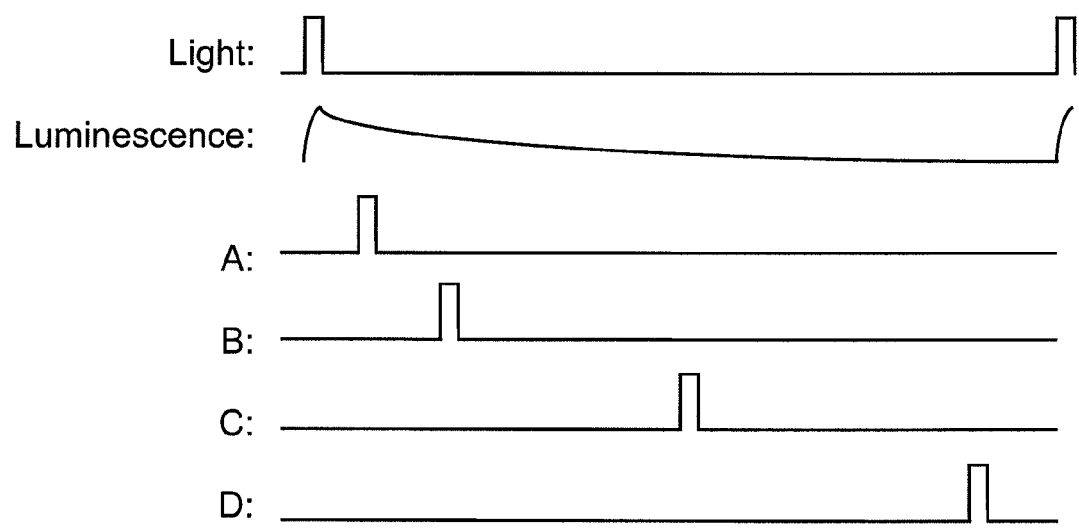
FIG. 6 is an approximate timing diagram relating to operation of the sensing apparatus.

FIG. 6 shows the timing (not to scale) of the operation of the light-emitting unit 14 and the accumulators 52A-52D. The timing and interface logic 38, under the control of the processor 40, causes the light-emitting unit 14 to emit an excitation pulse, which in this embodiment has a duration of 2.0 µs. During this excitation pulse, luminescence from the silica-gel particles 10 rapidly increases. After the pulse ends, the luminescence dies away exponentially, as shown in FIG. 6. The concentration of oxygen at the probe tip can be inferred from the rate of this exponential decay, which the present apparatus can determine.

The signal from the photo-detector 26, which is a voltage corresponding to the light intensity, is coarsely corrected for ambient light and is amplified by the amplifier 48, before being switched, for optimally positioned periods of time as described above, to one of the four accumulators 52A-52D by the operation of the switches 50A-50D, under the control of the timing and interface logic 38. In one configuration, the amplified signal is switched to the first accumulator 52A during the period 0.5 to 2.5 µs after the end of the excitation pulse; it is subsequently switched to the second accumulator 52B during the period 2.5 to 4.5 µs after the excitation pulse; then to the third accumulator 52C during the period 36.75 to 38.75 µs after the pulse; and finally to the fourth accumulator 52C during the period 145.5 to 147.5 µs after the pulse. These periods are indicated approximately in FIG. 6. The period for which each accumulator is active is thus 2.0 µs. The first two periods are consecutive, with no gap, and are where the rate of decay of the luminescence is relatively steep. The second two periods are spaced widely from the second period and from each other, and are in a region where the rate of decay is relatively shallow.

Other distributions of timing periods are, of course, possible. Typically, the distribution is determined by mathematical modelling which includes the lifetime characteristics of the sensor and the measurement range required in order to maximise accuracy while minimising noise. The configuration memory 42 can store several different configurations of timing regimes appropriate to the type of sensor connected, for different situations, which are read by the processor 40 as needed.

These may alternatively be stored in the processor itself; for example, in embodiments which do not have a separate configuration memory.

Once the luminescence has substantially died away, another excitation pulse is emitted, and the accumulators 52A-52D are again switched on during the same respective periods after each pulse. In the exemplary configuration above, excitation pulses are emitted every 150 microseconds.

This cycle of excitation pulses followed by switching of the accumulators is repeated typically a few thousand times (e.g. over an acquisition phase of 0.9 seconds). The decay curve may typically remain substantially the same for each excitation pulse throughout the acquisition phase, but in any event the method of processing will give an average lifetime for the acquisition phase. The output of each accumulator 52A-52D after the acquisition phase is thus a sum of integrals at respective positions along the exponential decay curve.

Figure 7:
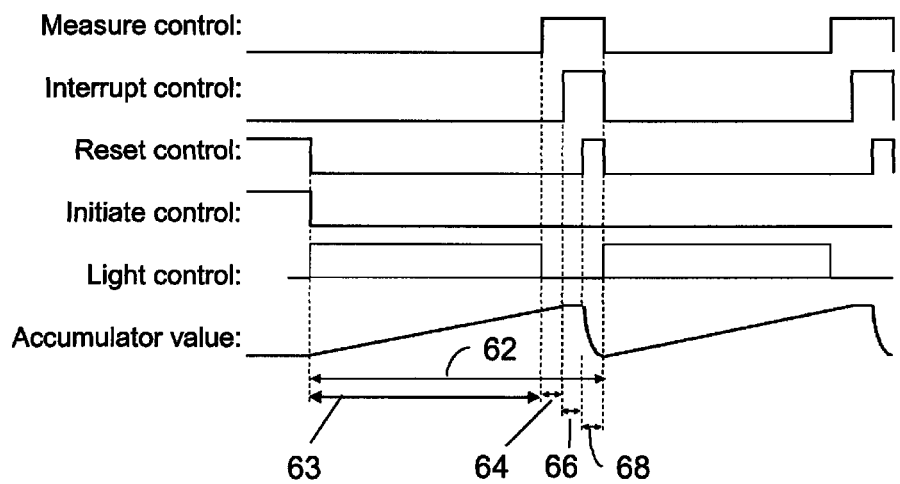
FIG. 7 is a further approximate timing diagram relating to operation of the sensing apparatus.

FIG. 7 shows the operation of the timing and interface logic 38 during two complete measurement cycles 62, each lasting about one second. Each measurement cycle 62 consists of an acquisition phase 63 of about 0.9 seconds, followed by a measurement phase consisting of a wait period 64 in which the decay from the final light pulse of the acquisition period is allowed to die away, followed by a read period 66, in which the values of the accumulators are read, and ending with a reset period 68 of about 0.05 seconds, in which the capacitors 58 in the accumulators 52A-52D are reset. The wait period 64 and the read period 66 total about 0.05 seconds.

Although the various phases may be timed quite differently in other embodiments, it is preferred in at least some embodiments that an acquisition phase lasts for about 90% of the total measurement cycle, with a subsequent read period of about 5% of the cycle, where no pulses or accumulation takes place, and finally a reset period of about 5% of the cycle in which the accumulators are reset to a zero value.

In detail, at the start of operation, an initiate control line is taken low, triggering the timing of all the other events. Immediately after initiation, a reset control line is taken low, causing the reset switches 60 in the accumulators 52A-52D to open. This allows the capacitors 58 in the accumulators 52A-52D to store charge and causes the accumulators to start integrating their input signal voltages. Simultaneously with this, a light control trigger in the timing and interface logic 38 causes the light-emitting unit 14 to be pulsed at a predetermined rate. During this acquisition phase 63, the output signal voltages of the accumulators 52A-52D are the integral over time of their input signal voltages. A graph of a typical accumulator output signal is shown in FIG. 7. In practice, the output value rises in steps, as the output of the photo-detector is switched periodically to each accumulator; however, over many repetitions (typically thousands within a single acquisition phase), the output value can be considered to rise substantially linearly as shown.

A measurement control line signals the end of the acquisition phase 63. The light-emitting unit ceases output and a wait period 64 commences. This allows the decay due to the final light pulse to be recorded by the accumulators 52A-52D. The end of the wait period 64 and the start of the read period 66 is signalled by an interrupt signal on the interrupt control line 43 from the timing and interface logic 38 to the processor, causing the processor 40 to interrupt and read each accumulator 52A-52D value in turn using the analogue-to-digital converter 36, and to store the result for later processing. At the same time, the timing and interface logic 38 uses the integration control lines 39A-39D to set all the switches 50A-50D to the accumulators 52A-52D open, so that the accumulators receive no more input signals. The accumulator output signals therefore remain steady and can be read by the analogue-to-digital converter 36. The digitised values are read sequentially by the processor 40 for analysis as described below. A reset control line then signals the end of the read period 66 and the start of a reset period 68 during which the switches 60 in the accumulators 52A-52D are closed in order to discharge the capacitors 58 in the accumulators, thereby resetting them.

After the accumulators 52A-52D have been reset, the measurement control line drops low, taking the interrupt control and reset control with it and signalling the start of a second measurement cycle. The light control line causes the light-emitting unit 14 to start pulsing again and the process repeats.

In an alternative embodiment, instead of reading the accumulator 52A-52D output signal levels once per measurement cycle, after the end of the acquisition phase 63, the timing and interface logic 38 interrupts the processor 40 on several occasions throughout the measurement cycle causing it to read the output of each accumulator on each occasion; this preferably occurs at a fixed sampling rate, e.g. at around 200 Hz. The processor stores each value along with a timestamp and a state value indicating where in the measurement cycle the reading was taken (e.g. whether it is an initial value, a rising value, a final value, or a value obtained during the reset period allocated for dielectric absorption immediately after the end of the reset control line pulse).

For each accumulator, the processor 40 can compute an average of any final-value readings, and these values can be used as the accumulator outputs in subsequent calculations.

Alternatively, the series of readings throughout the acquisition phase can be used by the processor 40 to estimate the slope of the substantially-linear rise in output value; this may involve, for example, performing a linear least-squares operation. Before this operation, however, any readings that are above a predetermined saturation value for the accumulator, or which are later in time than such a reading, can be discarded, thereby overcoming the problem of false readings from any accumulator that has reached a point of saturation and consequent phase reversal (some op-amps that may be used in the accumulators 52A-52D experience phase reversal when in saturation, such that the output of the op-amp can reduce below the saturated value while still in saturation; the output is then acting nonlinearly and will give rise to erroneous readings if not eliminated). This gradient value can then be used to compute a theoretical final output value by multiplying the gradient by the time between the end of the reset control signal and the start of the start of the interrupt control signal. The processor may also still compute an average of any final-value readings, and compare this with the result.

If there is an inconsistency, for example because the accumulator saturated during the measurement cycle, the theoretical final value can be used in place of the measured value. If an accumulator has not been ideally reset to zero, the theoretical final value should still be correct, while the measured value will be in error. In tests, using a calculated theoretical final value instead of a measured value, has proved to give good results notwithstanding the fact that the exponential luminescence lifetime might, in practice, vary slightly from one light pulse to another.

The processor 40 may perform any of these calculations at any time, but in some arrangements it does so during the reset period when it need not be sampling accumulator values.

Figure 8:
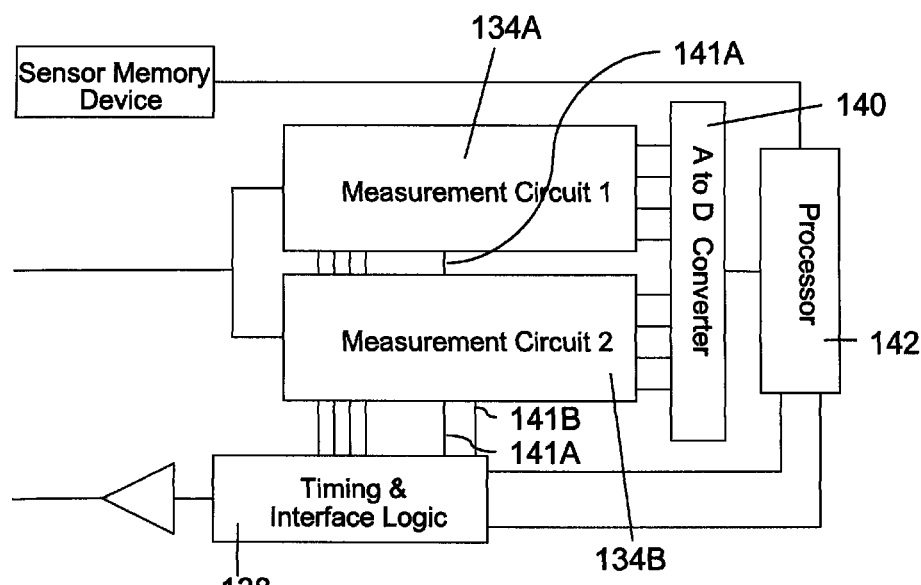
FIG. 8 is a schematic diagram of components within a second sensing apparatus embodying the invention.

FIG. 8 shows a third embodiment, similar to that of FIG. 3, but having a first measurement circuit 134A and a second, identical measurement circuit 134B. Each of these circuits is identical to the measurement circuit 34 of the previous embodiments. Each measurement circuit has its own accumulator control lines and reset control lines 141A, 141B. This embodiment has a total of eight accumulators, controlled as two blocks of four by the timing and interface logic 138. This allows a higher sampling rate than the previous embodiments, since the two blocks can be reset independently of each other. There is an A to D converter 140 and a processor 142.

Figure 9:
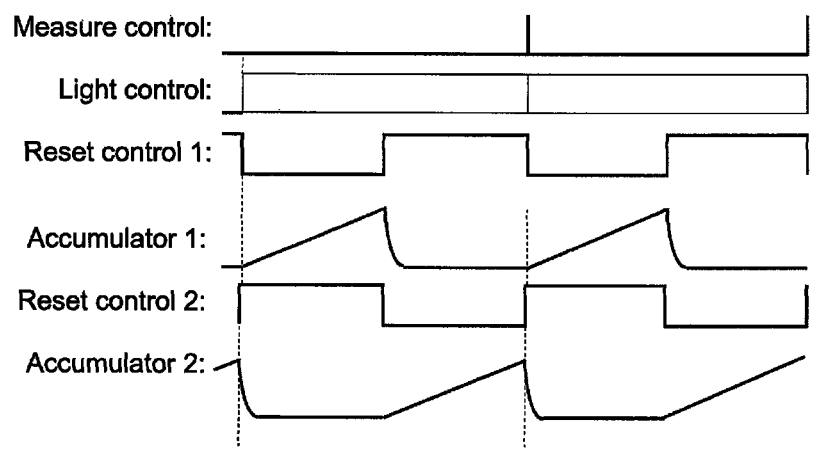
FIG. 9 is an approximate timing diagram relating to operation of the second sensing apparatus.

FIG. 9 illustrates the operation of this embodiment by showing two adjacent measurement cycles. In contrast to the previous embodiments, the light-emitting unit 14 pulses constantly, and the measurement line only pulses briefly to signal the start of each new measurement cycle. At the start of a measurement cycle, the first measurement circuit 134A is feed the output of the photo-detector 26 and switches this between its four accumulators. The output voltage of a typical accumulator 1 of this first measurement circuit is shown in FIG. 9; as before, it rises substantially linearly as it receives luminescence from successive light pulses. At the same time, a reset control line 2 for the second measurement circuit 134B is held low, causing the capacitors in the accumulators of the second circuit 134B to discharge. Part way through the measurement cycle, the reset control line 1 of the first circuit 134A is taken high, causing its accumulators to reset, and at the same time the reset control line 2 of the second circuit 134B is taken low, causing its accumulators to start integrating.

No wait and read periods are illustrated here, but they may be present in practice. However, if the accumulator output values are sampled throughout the acquisition phases, as explained above, it is possible to dispense with a final read period altogether.

Because the accumulators of one or other of the measurement circuits 134A, 134B are always active, this embodiment allows changes in assay concentration to be determined faster than the typical one second.

In all of the embodiments, it is desirable to calibrate each accumulator before using it, due to manufacturing tolerances between components in each accumulator. The apparatus is therefore arranged so that the connection 30 into the measurement circuit can, under the control of the processor 40, be fed by known, constant input signals, in place of the output of the photo-detector 26. The accumulator values recorded while a calibrated input is connected are then used to derive calibration coefficients to correct for any component tolerances.

Once theoretical or actual final values of each of the four accumulators have been determined for a measurement cycle, these are used by the processor 40 to derive an estimate of the lifetime of the exponential decay. The four values can be used to derive point values on the decay curve by dividing by the number of samples and the width of the switching period. The final estimate of the exponential decay lifetime is arrived at by assuming that it lies in some range. A spread of values in the range is tested and the range is subsequently refined as a result of the tested values. These steps are repeated until a sufficiently-accurate lifetime estimate is arrived at. More detail of this process is given below.

For a given lifetime $\tau$, the curve to be fitted is an exponential of the form $$f(t) = Ae^{\frac{-t}{\tau}} + B \quad (1)$$

where A is a scaling factor and B is an offset.

A set of point values $\{(Y_1,t_1),(Y_2,t_2),(Y_3,t_3)\ldots,(Y_n,t_n)\}$ can be expressed as $$Y_i = Ae^{\frac{-t_i}{\tau}} + B + \varepsilon_i \quad (2)$$

where $\varepsilon_i$ is the magnitude of the error of the actual value from the corresponding value on the curve.

The sum $\varepsilon_i^2$ can be written as $$\sum_{i=1}^{n} \varepsilon_i^2 = \sum_{i=1}^{n} \left(Y_i - Ae^{\frac{-t_i}{\tau}} - B\right)^2 \quad (3)$$

To fit the curve, the objective is to find values A and B that minimise the least squares error term $\Sigma\varepsilon^2$.

Differentiating the error term with respect to A and then to B and looking for stationary point gives $$\frac{\delta \sum_{i=1}^{n} \varepsilon_i^2}{\delta_A} = 2\sum_{i=1}^{n} \left[\left(Y_i - Ae^{\frac{-t_i}{\tau}} - B\right)\left(-e^{\frac{-t}{\tau}}\right)\right] = 0 \quad (4)$$

and $$\frac{\delta \sum_{i=1}^{n} \varepsilon_i^2}{\delta B} = 2\sum_{i=1}^{n} \left(Y_i - Ae^{\frac{-t_i}{\tau}} - B\right) = 0. \quad (5)$$

Simplifying gives $$\sum_{i=1}^{n} Y_i = A\sum_{i=1}^{n} e^{\frac{-t_i}{\tau}} + nB \quad (6)$$

and $$\sum_{i=1}^{n} Y_i e^{\frac{-t_i}{\tau}} = A\sum_{i=1}^{n} e^{\frac{-2t_i}{\tau}} + B\sum_{i=1}^{n} e^{\frac{-t_i}{\tau}}. \quad (7)$$

Solving for A and B then gives $$A = \frac{n\sum_{i=1}^{n} Y_i e^{\frac{-t_i}{\tau}} - \sum_{i=1}^{n} Y_i \sum_{i=1}^{n} e^{\frac{-t_i}{\tau}}}{n\sum_{i=1}^{n} e^{\frac{-2t_i}{\tau}} - \left(\sum_{i=1}^{n} e^{\frac{-t_i}{\tau}}\right)^2} \quad (8)$$

and $$B = \frac{\sum_{i=1}^{n} Y_i \sum_{i=1}^{n} e^{\frac{-2t_i}{\tau}} - \sum_{i=1}^{n} e^{\frac{-t_i}{\tau}} \sum_{i=1}^{n} Y_i e^{\frac{-t_i}{\tau}}}{n\sum_{i=1}^{n} e^{\frac{-2t_i}{\tau}} - \left(\sum_{i=1}^{n} e^{\frac{-t_i}{\tau}}\right)^2}. \quad (9)$$

In this way, it is possible for the processor 40 to determine the parameters A and B that give a best fit to the measured data for any given estimate $\tau$ of the exponential decay. The quality of the fit can be determined from the magnitude of the sum of squares error term as given in equation (3).

Although the present embodiments have shown four accumulators in a block, it will be understood that any number of accumulators may be used. The value of n in the present equations can be changed to reflect the number of accumulators without altering the validity of the equations.

A specific worked example of determining A and B now follows.

The objective is to minimise the sum of the squares of the errors, $\Sigma\varepsilon^2$, for a given value of $\tau$. Consider the case of four integrating windows, each of duration of 2 microseconds. The integrating windows are always positioned at 0.5, 2.5, 36.75 and 145.5 microseconds after the end of each excitation pulse. The time between excitation pulses is 150 microseconds.

The final accumulator values (either measured final accumulator values or calculated values using linear gradients) for each integration window and their corresponding timings are:

| t1 = 0.5 | t2 = 2.5 | t3 = 36.75 | t4 = 145.5 | (microseconds) |
|---|---|---|---|---|
| Y1 = 7.5351 | Y2 = 7.2802 | Y3 = 4.5942 | Y4 = 1.8993 | (Volts or Volts per seconds as applicable) |

Assume an estimate of lifetime $\tau$=75 microseconds.
For simplicity of notation, $$\text{Term 1} := \sum_{i=1}^{n} e^{\frac{-t_i}{\tau}}, \text{ Term 2} := \sum_{i=1}^{n} e^{\frac{-2t_i}{\tau}},$$

$$\text{Term 3} := \sum_{i=1}^{n} Y_i e^{\frac{-t_i}{\tau}} \text{ and Term 4} := \sum_{i=1}^{n} Y_i.$$

Then
Term $1 = e^{(-0.5/75)} + e^{(-2.5/75)} + e^{(-36.75/75)} + e^{(-145.5/75)} = 2.716901951$;
Term $2 = e^{(-1/75)} + e^{(-5/75)} + e^{(-73.5/75)} + e^{(-291/75)} = 2.318224071$;
Term $3 = 7.5351e^{(-0.5/75)} + 7.2802e^{(-2.5/75)} + 4.5924e^{(-36.75/75)} + 1.8993e^{(-145.5/75)} = 17.61402482$; and
Term $4 = 7.5351 + 7.2802 + 4.5924 + 1.8993 = 21.3088$.
Introducing these into equations (8) and (9) gives $$A = \frac{n \times Term3 - Term4 \times Term1}{n \times Term2 - (Term1)^2}$$
$$= \frac{(4 \times 17.61402482) - (21.3088 \times 2.716901951)}{(4 \times 2.318224071) - 2.716901951^2}$$
$$= 6.641946192$$

-continued and $$B = \frac{Term4 \times Term2 - Term1 \times Term3}{n \times Term2 - (Term1)^2}$$

$$= \frac{(21.3088 \times 2.318224071) - (2.716901951 \times 17.61402482)}{(4 \times 2.318224071) - 2.716901951^2}$$

$$= 0.815820859.$$

Then the sum of squares of the errors, $$\Sigma \varepsilon^2 = (7.5351 - Ae^{(-0.5/75)} - B)^2 + (7.2802 - Ae^{(-2.5/75)} - B)^2 +$$
$$(4.5924 - Ae^{(-36.75/75)} - B)^2 + 1.8993 - Ae^{(-145.5/75)} - B)^2$$
$$= 0.117489577$$

This is not the overall least squares fit to the data, but rather the best least squares fit for the given value of lifetime, $\tau=75$ microseconds.

In order to find an accurate estimate of the decay lifetime, an initial assumption of the lifetime must be made. First, the maximum and minimum possible acceptable lifetimes are defined. Once the likely range of luminescence lifetime is known for a dye, and the light pulse and accumulation periods and their relative positions have been optimised for the required measurement range, the upper and lower lifetime limits can be chosen. In one example, a minimum lifetime, $\tau_0$, is defined as being a tenth of the duration of an accumulation switching period, e.g. 0.2 microseconds, and the maximum lifetime, $\tau_4$, as being the time between successive light pulses, e.g. 150 microseconds.

The following algorithm is then performed, this being only one example of possible refinement algorithms:

1. Define five coefficients $\tau_0, \tau_1, \tau_2, \tau_3, \tau_4$
2. Set $\tau_0 :=$ the minimum lifetime limit
3. Set $\tau_4 :=$ the maximum lifetime limit
4. Set $\tau_2 := (\tau_0 + \tau_4)/2$
5. For a desired number of iterations do:
   a. Set $\tau_1 := (\tau_0 + \tau_2)/2$
   b. Set $\tau_3 := (\tau_2 + \tau_4)/2$
   c. For each of $\tau_0, \tau_1, \tau_2, \tau_3, \tau_4$ determine $\Sigma \varepsilon^2$
   d. If $\tau_0$ gives the smallest $\Sigma \varepsilon^2$ then $\tau_4 := \tau_1, \tau_2 := (\tau_0 + \tau_4)/2$
   e. If $\tau_1$ gives the smallest $\Sigma \varepsilon^2$ then $\tau_4 := \tau_2, \tau_2 := \tau_1$
   f. If $\tau_2$ gives the smallest $\Sigma \varepsilon^2$ then $\tau_0 := \tau_1, \tau_4 := \tau_3$
   g. If $\tau_3$ gives the smallest $\Sigma \varepsilon^2$ then $\tau_0 := \tau_2, \tau_2 := \tau_3$
   h. If $\tau_4$ gives the smallest $\Sigma \varepsilon^2$ then $\tau_0 := \tau_3, \tau_2 := (\tau_0 + \tau_4)/2$
6. Output $\tau_2$ as the final estimate.

If $\tau_2$ equals either of the minimum and maximum lifetime limits then the least-squares minimum is outside the range defined by the minimum and maximum limits.

The uncertainty in the final lifetime estimate is determined by the values of the minimum and maximum limits and the number of iterations, as follows:

$$\text{uncertainty} = (\text{maximum limit} - \text{minimum limit})/2^{(\text{iterations}-1)}. \quad (10)$$

The number of iterations can therefore be determined to give a required level of uncertainty in the lifetime estimate.

The likelihood of a numeric overflow is limited since the primary cause would be the determination of the exponential, which in this algorithm is limited to the range of the minimum and maximum limits.

A specific worked example of applying this algorithm to arrive at a least squares solution now follows. The numerical values are taken from the worked example above.

The integration pulse width effectively places a limit on the minimum lifetime which, in this case, shall be defined to be 0.05 microseconds. This is a fraction of the integration pulse width and gives the minimum limit $\tau_0$. Given that the time between pulses is 150 microseconds, it is reasonable to assume that the lifetime will be no greater than 150 microseconds, and the maximum limit, $\tau_4$, shall be defined to equal this.

From $\tau_0=0.05$ µs and $\tau_4=150$ µs, the algorithm gives $\tau_2=75.025$ µs. $\tau_1$ and $\tau_3$ are then calculated as the mid-points according to the algorithm. The first line in the table of FIG. 11 shows these values. Subsequent lines show successive steps of the iterative process of refining the values of $\tau_0$-$\tau_4$. The calculation of the exponential least-squares fit is as described above. The lines marked SSQ show the sum of the squares of the errors. The middle of the three SSQ values in the emphasised boxes is always the minimum SSQ for that iteration; it is repeated in the column to the right for clarity. Uncertainty is calculated as given above. The arrows indicate how the exponential lifetimes, $\tau$, and SSQ values are moved from one iteration to the next iteration.

The final output value from this example is therefore a lifetime $\tau=54.84$ (two decimal places).

Once an estimate of the luminescence lifetime has been generated, the concentration of oxygen can be determined using the Stern-Volmer equation $$\frac{\tau_{zero}}{\tau} = 1 + k_{SV}[Q] \quad (11)$$

where $\tau$ is the lifetime for the measured concentration, $\tau_{zero}$ is the lifetime at zero concentration, $k_{SV}$ is the Stern-Volmer constant, and Q is the concentration of oxygen.

This equation can be improved by adding a Langmuir isotherm to better reflect the actual data, giving $$\frac{\tau_{zero}}{\tau} = 1 + k_{SV}[Q]\alpha \frac{Kp}{1+Kp} \quad (12)$$

where K is the Langmuir constant, p is the partial pressure of oxygen, and $\alpha$ is an amalgamation of several constants.

Simplifying, a linear form relating the reciprocal of p to the reciprocal of $(\tau_0/\tau-1)$ can be obtained thus:

$$\frac{1}{p} = D \frac{1}{\left(\frac{\tau_{zero}}{\tau} - 1\right)} + C \quad (13)$$

where D and C in this equation are amalgamations of constant terms.

Where the deviation from the ideal Stern-Volmer equation is minimal, a broadly linear plot of the reciprocal of exponential lifetime against concentration is obtained. In order to allow for some deviation from this linear plot, a piecewise calibration scheme is employed.

Figure 10:
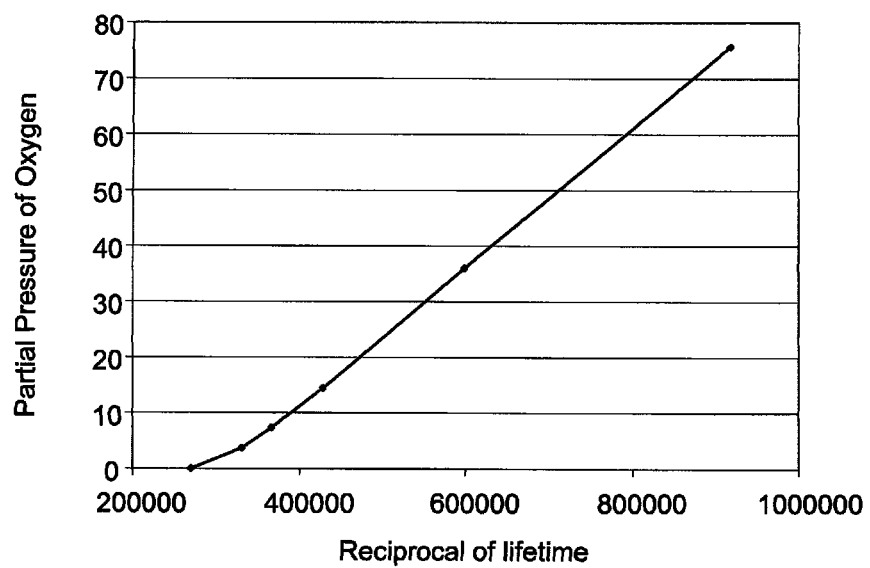
FIG. 10 is a graph relating partial pressure of oxygen to luminescent decay.

FIG. 10 shows a typical plot of partial pressure of oxygen against the reciprocal of exponential lifetime for a ruthenium luminescent dye.

To calibrate the sensor, the following steps can be performed:

expose the sensor to a range of assay substance concentrations over the desired range;

for each concentration, measure the luminescent lifetime; and record each data pair of assay concentration and lifetime in the configuration memory 42.

Where the performance of the luminophor is also dependent on temperature, this approach can be modified thus:

expose the sensor to a range of assay substance concentrations over the desired range of concentrations and temperatures;

for each concentration-temperature pair, measure the luminescent lifetime; and record each data triplet in the configuration memory 42.

Where a relationship can be found for extending calibration data to other temperatures without requiring further measurement, the data sets for unmeasured temperatures can be created and entered into the configuration memory 42 as if the data points had been measured empirically.

A simple method of sensor measurement, without temperature correction, is as follows:

extract the data from the configuration memory 42 and take the reciprocal of the luminescent lifetimes;

measure the sensor lifetime in the unknown assay substance concentration and take the reciprocal;

if the measured lifetime is outside the calibration data points, then determine the two nearest data sets;

if the measured lifetime is within the calibration data points, then determine the two calibration data sets either side of the measured lifetime;

calculate the line through the calibration data sets; and use the calculated line to convert the reciprocal of the measured exponential lifetime to the measured concentration.

A more complex method of sensor measurement, without temperature correction, is as follows:

extract the data from the configuration memory 42 and take the reciprocal of the luminescent lifetimes;

measure the sensor lifetime in the unknown assay substance concentration and take the reciprocal;

if the measured lifetime is outside the calibration data points, then determine the two nearest data sets and calculate the line through the calibration data sets;

if the measured lifetime is within the calibration data points, then determine the two calibration data sets either side of the measured lifetime and a third data set which is the nearest and calculate the parabola through the three calibration data sets; and use the calculated line or parabola to convert the reciprocal of the measured exponential lifetime to the measured concentration.

A simple method of sensor measurement with temperature correction is as follows:

extract the data from the configuration memory 42 and take the reciprocal of the luminescent lifetimes;

measure the sensor lifetime in the unknown assay substance concentration and take the reciprocal;

determine the three nearest calibration data sets with the proviso that all the points are not at the same temperature;

calculate the plane through the three calibration data sets; and use the calculated plane to convert the reciprocal of the measured exponential lifetime to the measured concentration.

In each of the embodiments above, the processor 40 has access to the non-volatile configuration memory 42. This configuration memory may store any of the following data:

sensor identification and configuration information;

the units of measurement for the assay substance;

the energy or time exposure of the sensor;

the allowed amount of energy or time exposure;

light pulsing and accumulator timings;

minimum and maximum acceptable luminescent lifetimes;

minimum and maximum acceptable sensor temperatures;

minimum and maximum acceptable assay concentrations; and sensor dye and temperature calibration information.

Recording the allowed and actual energy or time exposure of the sensor allows the state of photo-bleaching to be monitored and the sensor to be flagged as due for replacement when required.

The apparatus may comprise sensors incorporating conventional temperature measuring devices such as thermocouples with band-gap temperature sensors for cold junction correction. In such cases the configuration memory 42 may also store any of the following data:

Minimum and maximum un-calibrated cold junction temperatures; Minimum and maximum calibrated cold junction temperatures; Cold junction calibration information; Minimum and maximum thermocouple voltages; Minimum and maximum calibrated thermocouple temperatures; Thermocouple calibration information.

The use of the configuration memory 42 allows the instrument to be configured for a wide range of different situations. For example, sensors may be optimised for different measurement ranges, luminescent lifetimes and even different assay substances, all measured by the same apparatus. Although the description above refers to measuring oxygen concentration using a particular luminescent dye, it will be appreciated that properties and characteristics of substances other than oxygen may additionally or alternatively be measured by the same apparatus, perhaps with a different sensor probe attached, containing a different dye.

The invention may be viewed from a number of different aspects. Thus, viewed from a further aspect the invention provides a method of measuring the concentration of a substance, using a sensor comprising a luminescent material having a luminescent activity whose characteristics depend on the concentration of the substance, a light source which supplies a pulse of light to the sensor for a period of time sufficient to cause luminescence of the luminescent material, the luminescence rising to a peak and then decaying after the end of the pulse of light, a detector for detecting the light emitted by the luminescence of the luminescent material and generating signals in response thereto, and a data processing module for analysing the signals and for providing data indicative of the concentration of the substance; wherein in a measuring sequence there is a series of pulses of light spaced apart sufficiently to permit the luminescence to decay between pulses, the signals which are analysed to provide the data indicative of the concentration of the substance are those generated after each pulse of light has terminated and the luminescence is decaying, and wherein the data processing module comprises a plurality of accumulators which are controlled to be operable over a corresponding plurality of periods of time during decay of the luminescence, each accumulator accumulating a value indicative of the intensity of the luminescence after a pulse of light and accumulating the values from the series of pulses in the measuring sequence; and wherein for each accumulator the accumulator value is sampled at intervals during the measurement sequence, and the values are processed to provide a slope which is used in determination of the substance concentration.

Viewed from a further aspect the invention provides a method of measuring the concentration of a substance, using a sensor comprising a luminescent material having a luminescent activity whose characteristics depend on the concentration of the substance, a light source which supplies a pulse of light to the sensor for a period of time sufficient to cause luminescence of the luminescent material, the luminescence rising to a peak and then decaying after the end of the pulse of light, a detector for detecting the light emitted by the luminescence of the luminescent material and generating signals in response thereto, and a data processing module for analysing the signals and for providing data indicative of the concentration of the substance; wherein in a measuring sequence there is a series of pulses of light spaced apart sufficiently to permit the luminescence to decay between pulses, the signals which are analysed to provide the data indicative of the concentration of the substance are those generated after each pulse of light has terminated and the luminescence is decaying, and wherein the data processing module comprises two channels, each of which comprises a plurality of accumulators which are controlled to be operable over a corresponding plurality of periods of time during decay of the luminescence, each accumulator accumulating a value indicative of the intensity of the luminescence after a pulse of light and accumulating the values from the series of pulses in the measuring sequence; and wherein the measuring sequences are alternated between the two channels, the accumulators in one channel being reset after the end of the measuring sequence using that channel, whilst a measuring sequence is carried out using the other channel.

Viewed from a further aspect of the invention, there is provided method of measuring the concentration of a substance, using a sensor comprising a luminescent material having a luminescent activity whose characteristics depend on the concentration of the substance, a light source which supplies a pulse of light to the sensor for a period of time sufficient to cause luminescence of the luminescent material, the luminescence rising to a peak and then decaying after the end of the pulse of light, a detector for detecting the light emitted by the luminescence of the luminescent material and generating signals in response thereto, and a data processing module for analysing the signals and for providing data indicative of the concentration of the substance; wherein in a measuring sequence there is a series of pulses of light spaced apart sufficiently to permit the luminescence to decay between pulses, the signals which are analysed to provide the data indicative of the concentration of the substance are those generated after each pulse of light has terminated and the luminescence is decaying, and wherein the data processing module comprises a plurality of accumulators which are controlled to be operable over a corresponding plurality of periods of time during the decay of the luminescence, each accumulator detecting a value indicative of the intensity of the luminescence after a pulse of light and accumulating the values from the series of pulses in the measuring sequence.

Viewed from a further aspect, the invention provides apparatus for measuring the concentration of a substance, comprising a sensor comprising a luminescent material having a luminescent activity whose characteristics depend on the concentration of the substance, a light source which supplies a pulse of light to the sensor for a period of time sufficient to cause luminescence of the luminescent material, the luminescence rising to a peak and then decaying after the end of the pulse of light, a detector for detecting the light emitted by the luminescence of the luminescent material and generating signals in response thereto, and a data processing module for analysing the signals and for providing data indicative of the concentration of the substance; wherein the data processing module is configured so that in a measuring sequence there is a series of pulses of light spaced apart sufficiently to permit the luminescence to decay between pulses, the signals which are analysed to provide the data indicative of the concentration of the substance are those generated after each pulse of light has terminated and the luminescence is decaying, and wherein the data processing module comprises a plurality of accumulators which are controlled to be operable over a corresponding plurality of periods of time during decay of the luminescence, each accumulator accumulating a value indicative of the intensity of the luminescence after a pulse of light and accumulating the values from the series of pulses in the measuring sequence.

Viewed from a further aspect, the invention provides apparatus for measuring the concentration of a substance, comprising a sensor comprising a luminescent material having a luminescent activity whose characteristics depend on the concentration of the substance, a light source which supplies a pulse of light to the sensor for a period of time sufficient to cause luminescence of the luminescent material, the luminescence rising to a peak and then decaying after the end of the pulse of light, a detector for detecting the light emitted by the luminescence of the luminescent material and generating signals in response thereto, and a data processing module for analysing the signals and for providing data indicative of the concentration of the substance; wherein the data processing module is configured so that in a measuring sequence there is a series of pulses of light spaced apart sufficiently to permit the luminescence to decay between pulses, the signals which are analysed to provide the data indicative of the concentration of the substance are those generated after each pulse of light has terminated and the luminescence is decaying, and wherein the data processing module comprises a plurality of accumulators which are controlled to be operable over a corresponding plurality of periods of time during decay of the luminescence, each accumulator accumulating a value indicative of the intensity of the luminescence after a pulse of light and accumulating the values from the series of pulses in the measuring sequence; and wherein for each accumulator the accumulator value is sampled at intervals during the measurement sequence, and the values are processed to provide a slope which is used in determination of the substance concentration.

Viewed from a further aspect, the invention provides apparatus for measuring the concentration of a substance, comprising a sensor comprising a luminescent material having a luminescent activity whose characteristics depend on the concentration of the substance, a light source which supplies a pulse of light to the sensor for a period of time sufficient to cause luminescence of the luminescent material, the luminescence rising to a peak and then decaying after the end of the pulse of light, a detector for detecting the light emitted by the luminescence of the luminescent material and generating signals in response thereto, and a data processing module for analysing the signals and for providing data indicative of the concentration of the substance; wherein the data processing module is configured so that in a measuring sequence there is a series of pulses of light spaced apart sufficiently to permit the luminescence to decay between pulses, the signals which are analysed to provide the data indicative of the concentration of the substance are those generated after each pulse of light has terminated and the luminescence is decaying, and wherein the data processing module comprises two channels, each of which comprises a plurality of accumulators which are controlled to be operable over a corresponding plurality of periods of time during decay of the luminescence, each accumulator detecting a value indicative of the intensity of the luminescence after a pulse of light and accumulating the values from the series of pulses in the measuring sequence; and wherein the measuring sequences are alternated between the two channels, the accumulators in one channel being reset after the end of the measuring sequence using that channel, whilst a measuring sequence is carried out using the other channel.

Viewed from a further aspect of the invention, there is provided a software product for configuring a data processing module of apparatus for measuring the concentration of a substance, the apparatus comprising a sensor comprising a luminescent material having a luminescent activity whose characteristics depend on the concentration of the substance, a light source which supplies a pulse of light to the sensor for a period of time sufficient to cause luminescence of the luminescent material, the luminescence rising to a peak and then decaying after the end of the pulse of light, and a detector for detecting the light emitted by the luminescence of the luminescent material and generating signals in response thereto, the data processing module being for analysing the signals and for providing data indicative of the concentration of the substance, wherein the software product contains instructions which when run on the data processing module will cause the data processing module to operate so that in a measuring sequence there is a series of pulses of light spaced apart sufficiently to permit the luminescence to decay between pulses, the signals which are analysed to provide the data indicative of the concentration of the substance are those generated after each pulse of light has terminated and the luminescence is decaying, and wherein the data processing module comprises a plurality of accumulators which are controlled to be operable over a corresponding plurality of periods of time during decay of the luminescence, each accumulator accumulating a value indicative of the intensity of the luminescence after a pulse of light and accumulating the values from the series of pulses in the measuring sequence.

Viewed from another aspect of the invention, there is provided a software product for configuring a data processing module of apparatus for measuring the concentration of a substance, the apparatus comprising a sensor comprising a luminescent material having a luminescent activity whose characteristics depend on the concentration of the substance, a light source which supplies a pulse of light to the sensor for a period of time sufficient to cause luminescence of the luminescent material, the luminescence rising to a peak and then decaying after the end of the pulse of light, and a detector for detecting the light emitted by the luminescence of the luminescent material and generating signals in response thereto, the data processing module being for analysing the signals and for providing data indicative of the concentration of the substance, wherein the software product contains instructions which when run on the data processing module will cause the data processing module to operate so that in a measuring sequence there is a series of pulses of light spaced apart sufficiently to permit the luminescence to decay between pulses, the signals which are analysed to provide the data indicative of the concentration of the substance are those generated after each pulse of light has terminated and the luminescence is decaying, and wherein the data processing module comprises a plurality of accumulators which are controlled to be operable over a corresponding plurality of periods of time during decay of the luminescence, each accumulator accumulating a value indicative of the intensity of the luminescence after a pulse of light and accumulating the values from the series of pulses in the measuring sequence; and wherein for each accumulator the accumulator value is sampled at intervals during the measurement sequence, and the values are processed to provide a slope which is used in determination of the substance concentration.

Viewed from another aspect of the invention, there is provided a software product for configuring a data processing module of apparatus for measuring the concentration of a substance, the apparatus comprising a sensor comprising a luminescent material having a luminescent activity whose characteristics depend on the concentration of the substance, a light source which supplies a pulse of light to the sensor for a period of time sufficient to cause luminescence of the luminescent material, the luminescence rising to a peak and then decaying after the end of the pulse of light, and a detector for detecting the light emitted by the luminescence of the luminescent material and generating signals in response thereto, the data processing module being for analysing the signals and for providing data indicative of the concentration of the substance, wherein the software product contains instructions which when run on the data processing module will cause the data processing module to operate so that in a measuring sequence there is a series of pulses of light spaced apart sufficiently to permit the luminescence to decay between pulses, the signals which are analysed to provide the data indicative of the concentration of the substance are those generated after each pulse of light has terminated and the luminescence is decaying, and wherein the data processing module comprises two channels, each of which comprises a plurality of accumulators which are controlled to be operable over a corresponding plurality of periods of time during decay of the luminescence, each accumulator accumulating a value indicative of the intensity of the luminescence after a pulse of light and accumulating the values from the series of pulses in the measuring sequence; and wherein the measuring sequences are alternated between the two channels, the accumulators in one channel being reset after the end of the measuring sequence using that channel, whilst a measuring sequence is carried out using the other channel.

The features and optional features of any of these additional aspects of the invention may be used together and may be used in conjunction with features of the aspects of the invention discussed earlier.

The invention may also be used to measure the values of parameters other than concentration such as, for example, temperature or pH. Thus, viewed from another aspect the invention provides a method of measuring a parameter, using a sensor comprising a luminescent material having a luminescent activity whose characteristics depend on the value of the parameter, a light source which supplies a pulse of light to the sensor for a period of time sufficient to cause luminescence of the luminescent material, the luminescence rising to a peak and then decaying after the end of the pulse of light, a detector for detecting the luminescence and generating signals in response thereto, and a data processing module for analysing the signals and for providing data indicative of the value of the parameter; wherein there is a measuring sequence comprised of a series of pulses of light spaced apart sufficiently to permit the luminescence to decay between the pulses, the signals which are analysed to provide the data indicative of the concentration of the substance are those generated after each pulse of light has terminated and the luminescence is decaying, and wherein the data processing module comprises a plurality of accumulators which are controlled to be operable over a corresponding plurality of different periods of time during the decay of the luminescence, each accumulator accumulating values indicative of the intensity of the luminescence from the series of pulses in the measuring sequence.

The other aspects of the invention may be modified mutatis mutandis so as to refer to measurement of a parameter in general.

The invention claimed is:

1. A method of measuring the concentration of a substance, using a sensor comprising a luminescent material having a luminescent activity whose characteristics depend on the concentration of the substance, a light source which supplies a pulse of light to the sensor for a period of time sufficient to cause corresponding luminescence of the luminescent material, the luminescence rising to a peak and then decaying after the end of the pulse of light, a detector for detecting the light emitted by the luminescence of the luminescent material and generating signals in response thereto, and a data processing module for analyzing the signals and for providing data indicative of the concentration of the substance;

wherein in a measuring sequence there is a series of pulses of light spaced apart sufficiently to permit the luminescence corresponding to each pulse in the measuring sequence to decay between pulses, the signals which are analyzed to provide the data indicative of the concentration of the substance are those generated after each pulse of light has terminated and the corresponding luminescence is decaying, wherein the data processing module comprises a plurality of accumulators which are controlled to be operable over a corresponding plurality of different periods of time during the decay of the luminescence, wherein in an acquisition phase of the measuring sequence each accumulator accumulates intensity values indicative of the intensity of the luminescence corresponding to each of the series of pulses in the measuring sequence by adding the intensity value corresponding to one pulse to the accumulated values corresponding to previous pulses, and wherein the measuring sequence further comprises read phase in which the values accumulated in the accumulators are read and a reset phase after the acquisition and read phases in which the accumulators are reset.

2. A method as claimed in claim 1, wherein for each accumulator the accumulator value is sampled at intervals during the measuring sequence, and the values are processed to provide a slope which is used in determination of the substance concentration.

3. A method as claimed in claim 1, wherein the data processing module comprises two channels, each of which comprises a plurality of said accumulators which are controlled to be operable over a corresponding plurality of different periods of time during decay of the luminescence, each accumulator accumulating values indicative of the intensity of the luminescence from the series of pulses in the measuring sequence; and wherein the measuring sequences are alternated between the two channels, the accumulators in one channel being reset after the end of the measuring sequence using that channel, while a measuring sequence is carried out using the other channel.

4. A method as claimed in claim 1, wherein there are at least four accumulators, controlled to be operable over a corresponding number of different periods during the decay of the luminescence.

5. A method as claimed in claim 3 wherein in each channel there are at least four accumulators, controlled to be operable over a corresponding number of different periods during the decay of the luminescence.

6. A method as claimed in claim 1, wherein there are first and second accumulators which are timed to be active while the luminescence is decaying relatively steeply, the first accumulator being active over a first period of time and the second accumulator being active over an adjacent period of time which commences on, or a relatively short time after, the end of the first period of time.

7. A method as claimed in claim 6, wherein there is a third accumulator which is active over a third period of time, which commences a relatively long time after the end of the second period of time, when there is a substantially less steep rate of decay of the luminescence than during the first and second periods of time.

8. A method as claimed in claim 7, wherein there is a fourth accumulator which is active over a fourth period of time, which commences a relatively long time after the end of the third period of time.

9. A method as claimed in claim 1, wherein each accumulator is operable for a period which is less than 5 microseconds during the decay of the luminescence.

10. A method as claimed in claim 1, wherein the periods of time over which the respective accumulators are operable are of substantially equal duration.

11. A method as claimed in claim 1, wherein the periods over which the respective accumulators are active are determined by configuration parameters stored in a configuration memory.

12. A method as claimed in claim 11, wherein the configuration parameters are stored in a configuration memory which is part of the sensor, and when the sensor is connected to the control unit, a connection is made with the configuration memory, and the configuration parameters are read and used by the data processing module.

13. A method as claimed in claim 12, wherein the configuration memory which is part of the sensor stores, in addition to the configuration parameters, any or all of the energy and/or time exposure of the sensor;

the allowed amount of energy or time exposure;
the date of calibration of the sensor;
the allowed period of time from the date of calibration of the sensor;
the date of first use of the sensor;
the allowed period of time from the date of first use of the sensor;
the number of times that the sensor has been used;
the allowed number of times that the sensor may be used;
sensor identification information;
sensor configuration information;
the units of measurement for the assay substance;
light pulsing and accumulator timings;
minimum and maximum acceptable luminescent lifetimes;
minimum and maximum acceptable sensor temperatures;
minimum and maximum acceptable assay concentrations; and
sensor dye and temperature calibration information.

14. Apparatus for measuring the concentration of a substance, comprising a sensor comprising a luminescent material having a luminescent activity whose characteristics depend on the concentration of the substance, a light source which supplies a pulse of light to the sensor for a period of time sufficient to cause corresponding luminescence of the luminescent material, the luminescence rising to a peak and then decaying after the end of the pulse of light, a detector for detecting the light emitted by the luminescence of the luminescent material and generating signals in response thereto, and a data processing module for analyzing the signals and for providing data indicative of the concentration of the substance;

wherein the data processing module is configured so that in a measuring sequence there is a series of pulses of light spaced apart sufficiently to permit the luminescence corresponding to each pulse in the measuring sequence to decay between pulses, the signals which are analyzed to provide the data indicative of the concentration of the substance are those generated after each pulse of light has terminated and the corresponding luminescence is decaying, wherein the data processing module comprises a plurality of accumulators which are controlled to be operable over a corresponding plurality of different periods of time during decay of the luminescence, wherein in an acquisition phase of the measuring sequence each accumulator accumulates intensity values indicative of the intensity of the luminescence corresponding to each of the series of pulses in the measuring sequence by adding the intensity value corresponding to one pulse to the accumulated values corresponding to previous pulses, and wherein the measuring sequence further comprises a read phase in which values accumulated in the accumulators are read and a reset phase after the acquisition and read phases in which the accumulators are reset.

15. A method of measuring a concentration of a substance, using a sensor comprising a luminescent material having a luminescent activity whose characteristics depend on the concentration of the substance, wherein there is a measuring sequence having an acquisition phase and a reset phase;

during the acquisition phase a light source supplies a series of pulses of light to the sensor, each pulse of light causing a luminescence event in which there is luminescence of the luminescent material, the luminescence decaying over time after the pulse of light has ceased; there being a detecting system which detects light emitted by the luminescent material during each luminescence event and generates signals indicative of the intensity of the luminescence; wherein there is a plurality of accumulators which are controlled to be operable over a corresponding plurality of different periods of time during the decay of the luminescence in each luminescence event in the acquisition phase;

in respect of a first luminescence event in the acquisition phase, each accumulator receives and stores a value representing the intensity of the luminescence over the respective period of time for which the accumulator is operable;

in respect of a second luminescence event in the acquisition phase, each accumulator receives a second value representing the intensity of the luminescence over the respective period of time for which the accumulator is operable, which second value is added to the first value stored in the accumulator so as to provide an accumulated value stored in the accumulator;

in respect of each subsequent luminescence event in the acquisition phase, each accumulator receives a further value representing the intensity of the luminescence over the respective period of time for which the accumulator is operable, which further value is added to the existing stored value in the accumulator so as to provide a revised accumulated value;

at intervals in the acquisition phase the accumulated value in each accumulator is sampled;

for each accumulator the sampled values are processed to provide a slope;

after the acquisition phase there is a reset phase of the measuring sequence, in which the accumulators are reset; and wherein the substance concentration is determined using the slopes provided in the acquisition phase.

16. A method according to claim 15, wherein after the acquisition phase and the reset phase there is a further measuring sequence.

17. A method according to claim 15, wherein each sampled accumulated value is stored together with a state value indicating where in the measuring sequence the sample was taken.

18. A method according to claim 15, wherein the number of pulses in the series of pulses during the acquisition phase is of the order of thousands.

19. A method according to claim 18, wherein the accumulators are provided in a data processing module which comprises two channels, each of which comprises a plurality of said accumulators; and wherein the measuring sequences are alternated between the two channels, the accumulators in one channel being reset after the end of the measuring sequence using that channel, while another measuring sequence is carried out using the other channel.

\* \* \* \* \*